United States Patent [19]

Rich et al.

[11] 4,251,033

[45] Feb. 17, 1981

[54] MIST GENERATING STRUCTURE AND MOLDING APPARATUS THEREFOR

[75] Inventors: Michael Rich, Newtown; Konrad Eldracher, Startford, both of Conn.

[73] Assignee: Eastfield Corporation, Darien, Conn.

[21] Appl. No.: 914,885

[22] Filed: Jun. 12, 1978

[51] Int. Cl.³ .............................................. A61M 11/06
[52] U.S. Cl. ................ 239/338; 128/200.18; 128/200.21; 239/370; 261/78 A; 261/DIG. 65
[58] Field of Search ............... 239/338, 343, 370, 432; 128/194, 173 R, 200.18, 200.21; 261/DIG. 65, 78 A; 222/459, 565

[56] References Cited

U.S. PATENT DOCUMENTS

| | | | |
|---|---|---|---|
| 3,762,409 | 10/1973 | Lester | 128/194 |
| 3,826,255 | 7/1974 | Havstad et al. | 239/388 |
| 4,116,387 | 9/1978 | Kremer, Jr. et al. | 239/338 |

FOREIGN PATENT DOCUMENTS

| | | | |
|---|---|---|---|
| 1046264 | 12/1958 | Fed. Rep. of Germany | 239/338 |
| 640808 | 7/1950 | United Kingdom | 239/338 |

*Primary Examiner*—Johnny D. Cherry
*Assistant Examiner*—Michael J. Forman
*Attorney, Agent, or Firm*—Eugene E. Geoffrey, Jr.

[57] ABSTRACT

A mist generator for producing mists having uniformly fine particles which includes a housing having a base, a nozzle extending upwardly therefrom and a compressed gas inlet coupled to the nozzle and a cooperating structure disposed within the housing and engaging the nozzle, the cooperating structure having a plurality of successive chambers which function with the nozzle to aspirate a liquid retained in the base to form a mist and then effect agitation of the mist and, discharge it in a downward direction within the housing and an outlet on said housing for discharging the mist.

7 Claims, 7 Drawing Figures

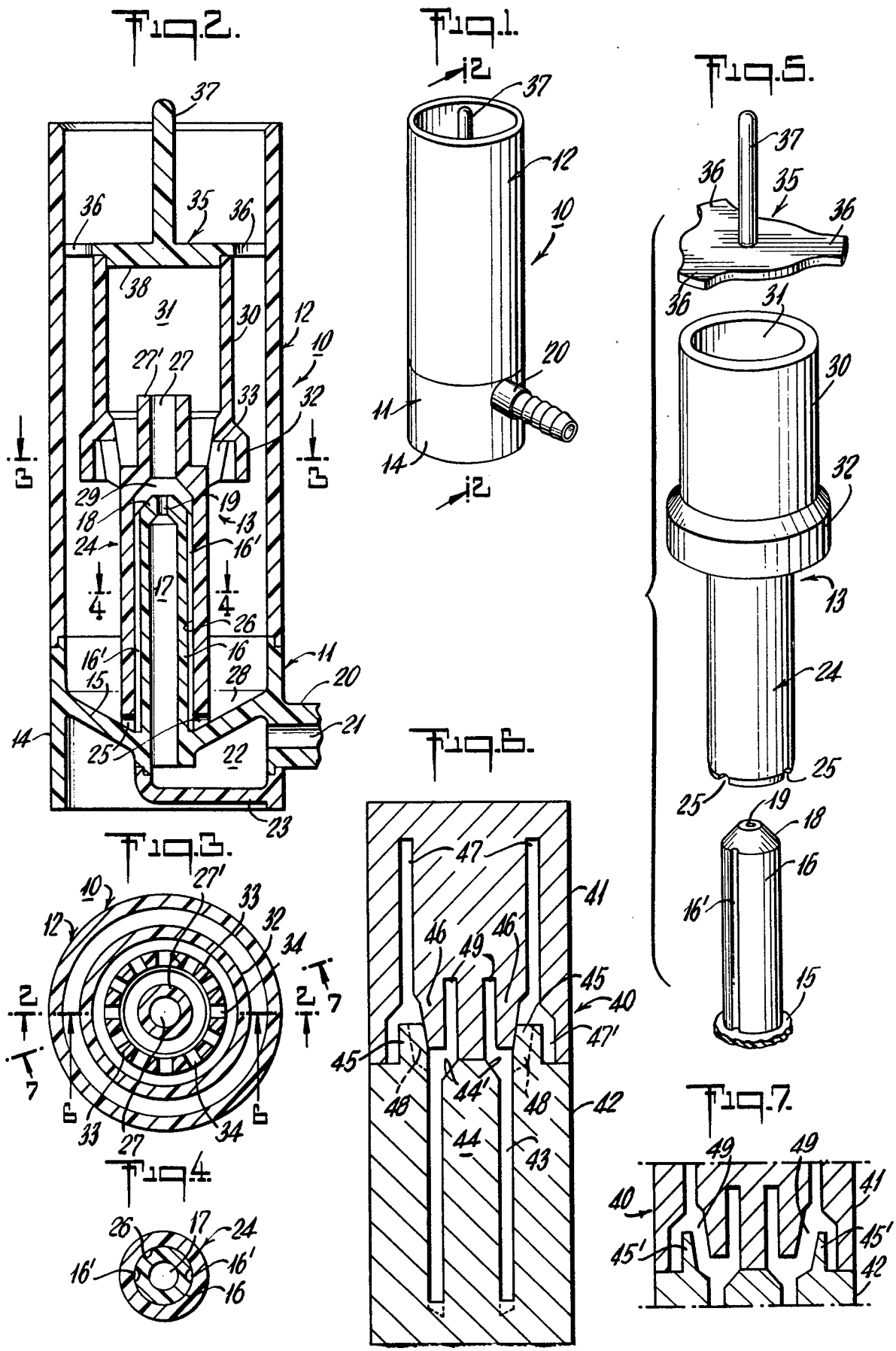

MIST GENERATING STRUCTURE AND MOLDING APPARATUS THEREFOR

This invention relates to nebulizers and more specifically to a novel and improved nebulizer structure and apparatus for the manufacture thereof for producing exceedingly fine mists useful among other things for various theropeutic and spraying applications.

One form of nebulizer or mist generator is disclosed in United States patent application Ser. No. 685,307, now Pat. No. 4,116,387, issued May 11, 1976, entitled MIST GENERATOR. The mist generator described in the foregoing application is formed of a number of components assembled in a manner that facilitates diassembly for cleaning and sterilization when necessary. Fabrication of the nebulizer is, however, relatively expensive and care is required in the assembly and disassembly of the parts within the housing.

This invention overcomes the foregoing difficulties and provides a novel and improved nebulizer wherein the housing, nozzle and compressed air inlet constitute one element and the cooperating mist generator constitutes a second element. Cleaning and sterilization can readily be effected, though by reason of the novel and improved arrangement of elements results in a materially reduced cost of manufacture which in many cases may be less than the cost of sterilization.

Another object of the invention resides in the provision of a novel and improved mist generator which affords improved operating characteristics and produces a uniformly fine mist.

Still another object of the invention resides in the provision of a novel and improved mold for forming a portion of the mist generator which greatly simplifies the manufacture thereof and materially reduces the cost.

Still another object of the invention resides in the provision of a novel and improved mist generator that may readily be fabricated of a variety of materials including metals and plastics.

The invention includes a two piece housing having a base portion with a nozzle extending upwardly therefrom and an upwardly extending wall portion secured to the base and surrounding the nozzle. The mist generator within the housing consists of a unitary structure having a tubular member surrounding the nozzle, an enlarged chamber coupled with the tubular member and having discharge openings at the lower portion thereof which are surrounded by a skirt. With this arrangement and with liquid in the base of the housing surrounding the nozzle, as compressed air is fed through the nozzle, liquid is aspirated to form a mist which is fed into the chamber and then discharged into the housing whereupon it passes upwardly through the housing outlet.

The above and other objects and advantages of the invention will become more apparent from the following description and accompanying drawings forming part of this application.

IN THE DRAWINGS:

FIG. 1 is a perspective view of one embodiment of a mist generator in accordance with the invention.

FIG. 2 is an enlarged cross-sectional view of the mist generator shown in FIG. 1 and taken along the lines 2—2 of FIGS. 1 and 3.

FIGS. 3 and 4 are cross-sectional views of FIG. 2 taken along the lines 3—3 and 4—4 thereof.

FIG. 5 is an exploded prospective view of the aspirator and the associated chambers disposed within the housing of the mist generator.

FIG. 6 is a cross-sectional view of two cooperating die sections for forming the central element of the mist generator as illustrated in FIG. 5 and is in the same plane as to the cross-section of the element shown in FIG. 2 and corresponds to a cross-section taken along the line 6—6 of FIG. 3.

FIG. 7 is a fragmentary section of the die shown in FIG. 6 wherein the cross-section has been shifted angularly to a position corresponding to the cross-section 7—7 of FIG. 3.

The illustrated embodiment of the mist generator, generally denoted by numeral 10, includes an outer housing consisting of a base 11 and an upper portion 12. The mist generating means within the housing is generally denoted by the numeral 13 as viewed in both FIGS. 2 and 5. This element is of unitary construction and is formed by the die as illustrated in FIGS. 6 and 7. In addition to the advantage of this mist generator construction which reduces the total number of pre-formed elements to five parts, the particular configuration of the generator produces an exceedingly fine substantially uniform mist having sub-micron particle sizes wherein the particles are all substantially below 0.1 microns.

More specifically, the instant embodiment of the invention comprises a base portion 11 having a cylindrical wall 14, a conical bottom wall 15 and a cylindrical nozzle 16, extending upwardly from the bottom wall 15. The nozzle has a central opening 17 which extends through the bottom wall 15. The upper portion 18 of the nozzle has a narrow opening 19 through which compressed air flows during the course of operation of the mist generator. An inlet 20 having a central opening 21 extends from the side of the base 11 and opens into a chamber 22 which is formed within the base 11 and closed by a cap 23. In this way compressed air upon being fed into the inlet 20 is discharged into chamber 22 whereupon it flows upwardly into the opening 17 and discharged through the nozzle opening 19. The chamber 22 functions as a low pass filter to provide a more uniform flow of air through the nozzle 16.

The mist generating means 13 as illustrated in FIGS. 2 and 5 is preferably formed as an integral unit and includes a lower tubular member 24 having recesses 25 in the bottom edge thereof. This member 24 has a central opening 26 and is designed to slidably engage the nozzle 16. The upper end of the opening 26 extends slightly beyond the forward end 18 of the nozzle and terminates in an elongated opening 27 in the tubular portion 27', the opening 27 having a diameter smaller than the diameter of the opening 24. With this arrangement, a chamber 28 is formed just in advance of the nozzle 16 so that compressed gas flowing through the nozzle and emerging from the opening 19 will draw liquid contained in the reservoir 28 by the conical bottom wall 15 upwardly throughchannels 16' formed in the outer surface in the wall of the nozzle 16 and produce a mist in the chamber 29 which then flows outwardly through the opening 27. The chamber 29 is preferably of coincal configuration as illustrated.

A tubular member 30 extends upwardly from the tubular member 24 and defines a mist receiving chamber 31. The tubular member 30 terminates at its lower end in a skirt or baffle 32 of somewhat enlarged diameter. The member 30 is peferably integrally joined to the tubular member 24 by annularly disposed elements 33 joined at their lower ends to the tubular members 24 and at their upper ends to the bottom edge of the tubular lar member 30. The annularly disposed elements 33 define a plurality of spaced openings 34 forming essentially rectangular openings for discharge of the mist from the chamber 31. The upper end of the tubular member 30 is closed by a cap 35 having outwardly extending legs 36 and a rod-like member 37 extending from the upper side thereof. The underside of the cap 36 has an annular portion 38 adapted to fit within the tubular member 30 and is preferably welded or otherwise secured thereto to form an airtight closure.

With the foregoing arrangement, the mist flowing through the opening 27 is discharged into the chamber 31 and then is caused to flow downwardly through the openings 34. By reason of the nature of the openings 34, the mist is directed essentially rearwardly or downwardly and then moves upwardly between the baffle 32 and the wall of the housing 12, whereupon it is discharged through the upper opening of the housing.

By reason of the arrangement and configuration of the openings 34, larger particles of the mist emerging from the opening 27 will tend to strike the walls of the chamber 31 and the resultant liquid can draim downwardly into the reservoir 28. Additional turbulence is produced by directing the mist downwardly through the rectangular openings and by reason of the direction of the mist the larger particles tend to continue the downward motion within the housing 12 while the finer particles will readily move upwardly and be discharged. The heavier particles in tending to continue their downward path will strike the wall of the housing whereupon the liquid will then return to the reservoir 28. With this arrangement an exceedingly fine mist is produced and the number of larger particles such as particles exceeding 0.1 microns is greatly reduced.

The die for producing the unitary structure 13, as illustrated in FIG. 2 and 5, is shown in FIGS. 6 and 7. FIG. 6 is a cross section of the die taken in the same plane as FIG. 2 (section 6—6 of FIG. 3) while the fragmentary section in FIG. 7 is taken in the plane angularly displaced from the plane of FIG. 6 (section 7—7 of FIG. 3). The die is generally denoted by the numeral 40 and consists of an upper portion 41 and a lower portion 42. The line of separation of the upper and lower die portions is defined by the cross-hatching which in the case of the lower portion is downwardly to the right and in the case of the upper portion is upwardly to the right.

The lower portion 42 of the die has a cylindrical bore 43 which forms the cylindrical portion 42 of the structure 13 and the upper end of the central core 44 is tapered as denoted by the numeral 44' to form the upper wall of the tapered chamber 29 as viewed in FIG. 2. An annular ring 45 extends upwardly from the die part 42 and includes a plurality of speed recesses 48 on the inner surface thereof. The inner surface of ring 45 cooperates with a downwardly extending ring 46 of the upper die portion 41 so that the recesses 45 form the spaced connecting elements 33 with the openings 34 therebetween through which the mist flows from the chamber 31 into the housing just prior to discharge through the upper opening in the housing. The upper die portion 41 has an annular bore 47 for forming the cylindrical portion 30 of the structure 13 while the annular space 47' between the outer surface of the ring 45 and the inner surface of the die portion 41 forms the skirt or baffle 32.

FIG. 7 which is taken along the lines 7—7 of FIG. 3 shows narrowed sections 45' of the ring 45 extending upwardly from the lower die portion 42. The narrowed sections 45' result from the formation of the recesses 48 in the ring 45. These recesses form a plurality inclined channels 49 in the die which ultimately form the spaced supports 33 as shown in FIG. 2 which are integrally joined with the upper and lower portions 30 and 24 of the structure 13. With this arrangement, the molded piece can be readily removed from the die. The annular bore 49 in the upper die portion 41 results in the formation of the annular structure 27' having a central opening 27 as illustrated in FIG. 2.

With the structure as described, the base 11 of the housing is integrally formed with the nozzle 16 and sonically welded or otherwise secured to the upper housing portion 12. The chamber 22 is then closed by a cap 23 as illustrated in FIG. 2 and the cap is welded or other wise secured permenantly thereto. The cap 35 as illustrated in FIGS. 2 and 5 is welded or otherwise secured to the top of the annular structure 30 in order to close the chamber 31. With this arrangement the resultant mist generator therefore consists of two elements, namely the complete housing and the structure 13 which can be easily positioned in place over the nozzle 16. For cleaning purposes as structure 13 is readily removed and sterilized along with the housing portion.

While only one embodiment of the invention has been illustrated and described it is understood that alterations and modifications may be made without departing from the ture scope and spirit thereof.

We claim:

1. A mist generator comprising means for producing a mist including a nozzle and a sleeve surrounding said nozzle, means forming at least one channel between said nozzle and said sleeve for aspirating a liquid when compressed air flows through said nozzle to produce a mist emanating from said sleeve, a tubular member defining a chamber above said sleeve, said sleeve extending into said chamber for discharging said mist at a point within said chamber, a plurality of spaced, radially disposed members each fixedly secured at one end to the upper portion of said sleeve and extending upwardly and outwardly therefrom, the other end of the last said members being fixedly attached to the lower portion of said tubular member and forming a plurality of outwardly and rearwardly directed openings for the discharge of said mist from said chamber, means closing the other end of said tubular member, and a housing surrounding said chamber and mist producing means and including an outlet for discharging said mist.

2. A mist generator according to claim 1 including a rearwardly opening baffle carried by said tubular member and surrounding said openings.

3. A mist generator according to claim 1 wherein said openings are of a generally rectangular configuration.

4. A mist generator comprising means for producing a mist, a tubular member defining a chamber, the first said means extending into said chamber for discharging said mist at a point within said chamber, a plurality of outwardly and rearwardly directed openings for the discharge of said mist, said means for producing said mist comprising an elongated nozzle including means for feeding a compressed gas therethrough, a sleeve slidably engaging said nozzle, said nozzle and sleeve having a liquid supplying channel therebetween, said sleeve extending beyond the end of said nozzle and terminating in tubular portion of reduced diameter at least partially disposed within said chamber, a plurality spaced radially disposed members fixedly secured at one end to the outer end of said sleeve and at the other end to the said tubular member, said radially disposed members defining said openings, means closing the outer end of said tubular member to form a closed chamber and a housing surrounding said nozzle and tubular member and sleeve and including an outlet for discharging the mist emerging from said openings.

5. A mist generator according to claim 4 wherein said radially disposed members are integrally formed with said tubular member and sleeve.

6. A mist generator according to claim 5 wherein said housing comprises a base having a conical bottom wall, said nozzle extends outwardly from said conical bottom, a gas inlet on said base beneath the conical wall and communicating with said nozzle and an upper housing portion firmly secured to said base.

7. A mist generator according to claim 5 wherein said tubular member and sleeve and said spaced radially disposed members constitute a unitary structure simultaneously formed in a single die.

* * * * *